United States Patent [19]

Kleemiss et al.

[11] Patent Number: 6,045,662
[45] Date of Patent: Apr. 4, 2000

[54] PROCESS FOR PREPARING HIGH-PURITY CYCLOPROPYL METHYL KETONE

[75] Inventors: Wolfgang Kleemiss, Haltern; Guenther Koehler; Manfred Neumann, both of Marl, all of Germany

[73] Assignee: Huels Aktiengesellschaft, Marl, Germany

[21] Appl. No.: 09/033,071

[22] Filed: Mar. 2, 1998

[30] Foreign Application Priority Data

Mar. 15, 1997 [DE] Germany ............ 197 10 879

[51] Int. Cl.⁷ ............ B01D 3/00; C07C 49/293
[52] U.S. Cl. ............ 203/80; 203/99; 203/DIG. 19; 568/338
[58] Field of Search ............ 203/99, DIG. 19, 203/71, 73, 80; 568/346, 338, 350

[56] References Cited

U.S. PATENT DOCUMENTS

| | | | |
|---|---|---|---|
| 5,254,739 | 10/1993 | Hunston et al. | 568/346 |
| 5,336,809 | 8/1994 | Böhm et al. | 568/354 |
| 5,629,455 | 5/1997 | Kaufhold et al. | 568/343 |
| 5,763,627 | 6/1998 | Kaufhold | 549/507 |

FOREIGN PATENT DOCUMENTS 0 552 586 A1  7/1993  European Pat. Off. .

OTHER PUBLICATIONS

Perry et al, "Distillation", Technique of Organic Chemistry, vol. IV, 1965, p. 3.

*Primary Examiner*—Virginia Manoharan
*Attorney, Agent, or Firm*—Oblon, Spivak, McClelland, Maier & Neustadt, P.C.

[57] ABSTRACT

A process for preparing high-purity cyclopropyl methyl ketone from compositions which contain cyclopropyl methyl ketone, 4,5-dihydro-2-methylfuran, addition products of 4,5-dihydro-2-methylfuran by a continuous rectification process in which at least a portion of the composition to be purified is introduced into a rectification apparatus via a side feed located above the bottom portion of the apparatus.

17 Claims, No Drawings

PROCESS FOR PREPARING HIGH-PURITY CYCLOPROPYL METHYL KETONE

BACKGROUND OF THE INVENTION

1. Field of the Invention

The present invention relates to a process for preparing high-purity cyclopropyl methyl ketone (CPMK) from compositions, e.g., reaction discharges or mixtures, that contain CPMK, 4,5-dihydro-2-methylfaran (DHMF), addition products of DHMF, and, optionally, impurities which are produced in the synthesis of CPMK from 2-acetylbutyrolactone (ABL).

2. Description of the Background

CPMK is a valuable intermediate which is required in high purity for the synthesis of a variety of agricultural and pharmaceutical active compounds. A purity of >99% by weight is required for the use of CPMK as a building block for synthesis in the agricultural and pharmaceutical sectors.

CPMK can be particularly advantageously prepared from ABL by cyclizing ABL to give CPMK with elimination of $CO_2$ under alkali metal halide catalysis [Chemistry Letters 11, pp. 1149–52 (1975)]. It may be prepared continuously by introducing the alkali metal halide in a solvent at high temperature and continuously adding the ABL. Since, in the reaction, in addition to the main product CPMK, DHMF is also formed at a content of usually 5 to 30% by weight, as product of value of the reaction, a mixture of CPMK and DHMF is always continuously distilled off simultaneously from the reaction. Corresponding preparation processes are disclosed, for example, in EP-A 0 552 586 or DE-A 195 03 241. However, the CPMK obtained in this manner does not comply with the desired purity requirements because of the unacceptably high DHMF content.

DHMF is sufficiently more volatile than CPMK and can therefore in principle be separated off from CPMK by distillation without problems, in order to obtain CPMK of high purity. However, in the presence of acid, DHMF reacts with numerous nucleophiles, such as water, alcohols, amines etc., to give high-boiling addition products (cf Houben/Weyl: Methoden der organischen Chemie [Methods in Organic Chemistry], Vol. VI/3, 1965, p. 698, incorporated herein by reference). The addition of water to DHMF forms, for example, acetopropanol, which itself can in turn add to DHMF. These addition reactions are reversible, so that at high temperatures acetopropanol or its addition product to DHMF or other addition products to DHMF can release DHMF again by elimination or cyclization.

In a crude mixture of CPMK and DHMF, small amounts of water or other nucleophilic impurities are also always present, which reversibly convert DHMF into high-boilers in the manner described above. Purification of CPMK by distillation to separate off DHMF, therefore leads, depending on the bottom temperature, to recleavage of the higher-boiling DHMF addition products and thus again to contamination of CPMK with DHMF in the final distillation fraction. In the purification of CPMK by distillation, there is therefore always the problem of contamination of the CPMK by recleavage of the addition products of DHMF as a function of the bottom temperature. Because of the bottom temperatures required in conventional distillations, e.g., 110 to 180° C., which are necessary to comply with the purity requirements, there is the necessity of separating off further DHMF from the first runnings and final fractions of the distillation. However, this requires a high technical complexity and reduces the CPMK yield.

Lowering the bottom temperature by applying a vacuum and thus preventing recleavage of DHMF addition products and the thus ensuing contamination of CPMK can be accomplished. However, the technical complexity for condensing the relatively low-boiling CPMK is too great, making this process unfeasible.

SUMMARY OF THE INVENTION

It is an object of the present invention to provide a simple process for preparing high-purity CPMK in very good yields, by purifying CPMK from a composition, e.g., a reaction discharge or mixture, which contains CPMK, DHMF, addition products of DHMF, and, optionally, impurities which are produced during the synthesis of CPMK from 2-acetylbutyrolactone (ABL).

The object of the present invention and others is achieved with a process for preparing high-purity cyclopropyl methyl ketone from a composition which contains CPMK, DHMF, and addition products of DHMF, by (a) introducing the composition into a rectification apparatus having a bottom and a side feed above the bottom through the side feed; and (b) rectifying the composition to produce purified cyclopropyl methyl ketone, where steps (a) and (b) are conducted simultaneously.

A more complete appreciation of the invention and many of the attendant advantages thereof will be readily obtained as the same becomes better understood by reference to the following detailed description.

DETAILED DESCRIPTION OF THE INVENTION

Surprisingly, using the process according to the present invention, high-purity CPMK having a purity of >99% by weight can be prepared in high yield. The purity may be 99.3% by weight or higher, such as 99.5% by weight. Yields of high-purity CPMK of over 90% (based on the CPMK content in the starting mixture to be worked up according to the invention) can be achieved according to the invention. Preferably, the yield is at least 93% by weight, more preferably at least 94% by weight, and, most preferably, at least 95% by weight.

The present invention includes a continuous rectification step in an apparatus having a bottom and a side feed located above the bottom. In the present process, at least a portion of the impure mixture containing CPMK is added to the rectification by means of the side feed, by means of which the amount of the mixture to be fractionated introduced in the bottom of the apparatus is significantly decreased in comparison with conventional, purely distillation, processes. A fraction of the impure composition may be added via the side feed. Alternatively, all of the impure composition is introduced through the side feed. The rectification step according to the invention each time of only a small portion of the starting mixture to be worked up according to the invention enables the bottom temperature, during the entire work-up of the starting mixture, possibly including further distillation process steps, to be lowered to less than or equal to 160° C., preferably less than or equal to 140° C., particularly preferably less than or equal to 120° C. This suppresses the recleavage of addition products of DHMF and facilitates the production of high-purity CPMK. The bottom temperature may be 110, 112, 115, 118° C., or lower.

The process according to the invention is very simple to carry out, since conventional rectification apparatuses can be used for the rectification step according to the invention. As already mentioned, the process according to the invention for the work-up of the starting mixture can comprise, in addition to this rectification step, other, e.g. distillation, process steps. For a general discussion of distillation processes, see *Kirk-Othmer Encyclopedia of Chemical Technology*, Volume 8, pp. 311–358, 1993, incorporated herein by reference.

In a preferred embodiment of the process according to the invention, initially, for example, a portion of the DHMF, which is more volatile than CPMK, may be distilled off from the starting mixture to be fractionated. This distillation may be performed continuously or batchwise at bottom temperatures preferably below 120° C. The resulting crude CPMK, which is still contaminated primarily with high-boiling addition products of DHMF and with other compounds which can result from the synthesis of CPMK from 2-acetylbutyrolactone (ABL), is fed into a distillation column at the side above the bottom. At the top of the column, in the steady state, CPMK is taken off at a purity of >99% by weight, with the bottom temperature not exceeding 160° C., preferably not exceeding 140° C., particularly preferably not exceeding 120° C. Based on the CPMK content in the starting mixture to be fractionated, yields of high purity CPMK by distillation of greater than 95% can be achieved.

In another particularly preferred embodiment, the process according to the invention comprises one single continuous rectification step for preparing high-purity CPMK. The starting mixture to be fractionated may be fed to the rectification apparatus in this case at the side roughly in the center of the column in such a manner that the ratio of the number of theoretical plates of the enrichment portion of the column to the number of theoretical plates of the stripping portion is 1 to 2. This ratio range includes all specific values and subranges therebetween, including 1.1, 1.2, 1.3, 1.4, 1.5, 1.6, 1.7, 1.8, and 1.9. At the top of the column, the low-boiling DHMF may be continuously separated off, whereas in a sidestream takeoff just above the distillation bottom phase, the CPMK may be obtained at a high purity >99% by weight and high yield of customarily greater than 90%. The sidestream takeoff of the CPMK is preferably performed immediately above the boiling liquid of the bottom; however, it can alternatively be performed in the lower third, based on the number of theoretical plates, of the stripping column in the vicinity of the bottom. Some of the bottom product can be taken off during the distillation, if required.

In practice, to carry out this last-mentioned particularly preferred process embodiment, distillation columns having arranged distillation packings have proved useful. Good results have been achieved, for example, using a column having a separation capacity of 25 theoretical plates, arranged in 3 sections, or a column having a separation capacity of 35 theoretical plates, arranged in 4 sections. The sidestream takeoff of the high-purity CPMK is performed here either below or above the 1 st packing above the bottom; the feed was arranged either at the center or near the bottom above the first of the total of 3 packings. The last-described single-stage preferred embodiment is suitable, in particular, for industrial application, because of its simple handling and practicability.

The process according to the invention is expediently carried out under atmospheric pressure, but can also be carried out at a pressure of 300 to 1050 mbar, preferably at 500 to 1030 mbar, particularly preferably at 800 to 1020 mbar.

Having generally described this invention, a further understanding can be obtained by reference to certain specific examples which are provided herein for purposes of illustration only and are not intended to be limiting unless otherwise specified.

EXAMPLES

Comparative Example

| | |
|---|---|
| Distillation feedstock: | 1239.3 g |
| Composition: | CPMK: 1080.7 g (87.2% by weight) |
| | DHMF: 137.6 g (11.1% by weight) |
| | Water: 7.4 g (0.6% by weight) |
| Apparatus: | 0.5 m Multifil distillation column |
| | 2 l distillation flask |
| Distillation: | The mixture to be rectified is introduced into the distillation stillpot. The mixture is heated to boiling using an oil bath. DHMF is first distilled off at a reflux ratio of 20:1. Then, >99% by weight pure CPMK is produced at a reflux ratio of 5:1. |
| | As a final fraction, at an elevated bottom temperature, a CPMK fraction contaminated with DHMF is obtained. |

The fractions listed in Table 1 are obtained.

TABLE 1

| Fraction | Oilbath temperature (° C.) | Bottom temp. (° C.) | Top temp. (° C.) | Reflux (R/D) | Mass (g) | GC (% by weight) | |
|---|---|---|---|---|---|---|---|
| | | | | | | DHMF | CPMK |
| 1 | 132–134 | 107–110 | 72–80 | 20:1 | 28.9 | 80.1 | 2.4 |
| 2 | 134–138 | 110–111 | 81–82 | 20:1 | 21.6 | 91.0 | 4.6 |
| 3 | 138–150 | 112–113 | 84–102 | 20:1 | 56.8 | 71.1 | 27.6 |
| 4 | 152–158 | 113–114 | 102–112 | 20:1 | 76.0 | 13.4 | 85.7 |
| 5 | 159 | 114–116 | 112 | 5:1 | 940.0 | 0.4 | 99.1 |
| 6 | 160–220 | 116–199 | 108–109 | 5:1 | 65.3 | 8.6 | 86.2 |
| Residue | | | | | 43.4 | | |
| Total | | | | | 1232.0 | | |

Fraction 5 is the product of value, i.e., contains CPMK. The distillation yield of 99% by weight pure CPMK is 86%, based on a starting amount of CPMK of 1080.7 g. As a final fraction, a CPMK fraction which is again heavily contaminated with DHMF (fraction 6) is obtained.

Example 1

According to the Invention, Two-Stage Distillation

| Distillation feedstock: | 1593.5 g |
|---|---|
| Composition: | CPMK: 1362.4 g (85.5% by weight)<br>DHMF: 200.8 g (12.6% by weight)<br>Water: 15.9 g (1.0% by weight) |
| Apparatus: | 1l distillation flask with side outlet, two heatable 0.5 m Multifil columns mounted one on top of the other, with central feed. | a) DHMF/Water Separation

Procedure

Approximately 500 g of the distillation feedstock are introduced into the k-k-k-- distillation flask. At a bottom temperature of 109 to 113° C. and a reflux ratio of 10:1, a DHMF/water mixture is first distilled off up to a top temperature of 83° C. The remaining distillation feedstock is then continuously fed into the center of the column at a rate of approximately 150 gfh. The overflowing distillation bottom phase is collected in a storage vessel.

Continuous Distillation Conditions:

Bottom temperature: 113–114° C.

Top temperature: 82–83° C.

Refklux (Rk/D): 12:1

After completion of the continuous distillation, the following are present:

| 1. Distillate: | 214.5 g | |
|---|---|---|
| Composition: | CPMK: | 20.3 g (9.5% by weight) |
| | DHMF: | 180.2 g (84.0% by weight) |
| | Water: | 14.0 g (6.5% by weight) |
| 2. Distillation bottom product: | 1378.0 g | |
| Composition: | CPMK: | 1342.0 g (97.4% by weight) |
| | DHMF: | 20.8 g (1.5% by weight) |
| | Water: | 1.9 g (0.1% by weight) |
| | Residue: | 13.3 g (1.0% by weight) | b) Purification of CPMK by Distillation (Rectification)

Distillation feedstock: Distillation bottom product from the preceding distillation (1378.0 g)

Procedure

Approximately 400 g of the distillation bottom product from the preceding DHMF/water separation are introduced into the above-described apparatus, the bottom outlet being closed. The purification by distillation is begun at a bottom temperature of 113° C. and a top temperature of 111° C. and the feed of the remaining distillation bottom product (150 gk/h) into the column center is then begun.

Continuous rectification conditions:

Bottom temperature: 113–114° C.

Top temperature: 112° C.

Reflux (R/D): 5:10

Two Fractions are Obtained as a Result

| Fraction 1: | 50.0 g comprising: | 98.0% by weight of DHMF and 1.5% by weight of CPMK |
|---|---|---|
| Fraction 2: | 1287.0 g comprising: | 99.5% by weight of CPMK |
| Residue: | 40.0 g | |

The yield of 99.5% by weight pure CPMK is thus 94.4%, based on the mass of CPMK in the original distillation feedstock.

Example 2

According to the Invention, Single-Stage Rectification

| Distillation feedstock: | 3971.9 g |
|---|---|
| Composition: | CPMK: 3654.1 g (92.2% by weight)<br>DHMF: 278.1 g (7.0% by weight)<br>Water: 35.7 g (0.9% by weight) |
| Apparatus: | 1l distillation three neck flask having two heatable 0.5 m Multifil columns mounted one on top of the other, with central feed and a distillation bridge mounted directly above the bottom. |

Procedure

At an oilbath temperature of 128° C., the distillation feedstock is fed into the center of the column at a rate of 150 g/h. DHMF is separated off at the top of the column (fraction K1), while CPMK is distilled over the distillation bridge.

Distillation conditions

Bottom temperature: 110–116° C.

Top temperature K1: 79–82° C.

Top temperature K2: 113° C.

Reflux R1, R/D: 50:1

Reflux R2, R/D: 1:2

| Fraction K1: | 304.0 g comprising | 87.2% by weight of DHMF, 1.6% by weight of CPMK and 11.1% by weight of water |
|---|---|---|
| Fraction K2: | 3418.8 g comprising | 99.5% by weight of CPMK |
| Residue: | 245.0 g | |

The overall yield of 99.5% by weight pure CPMK is thus 93.6%, based on the mass of CPMK in the distillation feedstock.

German Patent Application 197 10 879.2, filed Mar. 15, 1997, is incorporated herein by reference in its entirety.

Obviously, numerous modifications and variations of the present invention are possible in light of the above teachings. It is therefore to be understood that, within the scope of the appended claims, the invention may be practiced otherwise than as specifically described herein.

What is claimed as new and desired to be secured by Letters Patent of the United States:

1. A process for purifying cyclopropyl methyl ketone, comprising:

(a) introducing a composition containing cyclopropyl methyl ketone (CPMT(), 4,5-dihydro-2-methylfuran (DHMF), and addition products of 4,5-dihydro-2-methylfuran into a rectifcation apparatus having a bottom and a side feed above the bottom, wherein at least a portion of said composition is introduced through the side feed; and (b) rectifying the composition at a bottom temperature of less than or equal to 160° C. to distill off DHMF and produce purified cyclopropyl methyl ketone at the side stream, wherein steps (a) and (b) are conducted simultaneously such that the formation of recleavage addition products of DHMF is suppressed.

2. The process of claim 1, wherein the composition further comprises impurities produced during the synthesis of cyclopropyl methyl ketone from 2- acetylbutyrolactone.

3. The process of claim 1, wherein the bottom temperature is less than or equal to 140° C.

4. The process of claim 1, wherein the bottom temperature is less than or equal to 120° C.

5. The process of claim 1, further comprising prior to the rectification step, distilling the composition to separate off components which are more volatile than cyclopropyl methyl ketone.

6. The process of claim 1, comprising one rectifying step, wherein the rectification apparatus further comprises (1) a stripping column above the bottom and below the side feed and (2) an enrichment column above the side feed, the rectification apparatus further comprises a side stream takeoff in the lower third of the stripping column, and the ratio of the number of theoretical plates of the enrichment column to the number of theoretical plates of the stripping column is 1 to 2.

7. The process of claim 1, which is conducted at atmospheric pressure.

8. The process of claim 1, which is conducted at a pressure of 300 to 1050 mbar.

9. The process of claim 1, which is conducted at a pressure of 500 to 1030 mbar.

10. The process of claim 1, which is conducted at a pressure of 800 to 1020 mbar.

11. The process of claim 1, wherein the purified cyclopropyl methyl ketone has a purity of at least 99% by weight.

12. The process of claim 1, wherein the purified cyclopropyl methyl ketone has a purity of at least 99.3% by weight.

13. The process of claim 1, wherein the purified cyclopropyl methyl ketone has a purity of at least 99.5% by weight.

14. The process of claim 1, wherein the purified cyclopropyl methyl ketone is at least 90% by weight, based on the weight of cyclopropyl methyl ketone in the composition.

15. The process of claim 1, wherein the purified cyclopropyl methyl ketone is at least 93% by weight, based on the weight of cyclopropyl methyl ketone in the composition.

16. The process of claim 1, wherein the purified cyclopropyl methyl ketone is at least 95% by weight, based on the weight of cyclopropyl methyl ketone in the composition.

17. The process according to claim 1, wherein the addition products of 4,5-dihydro-2-methylfuran comprise acetopropanol, the addition product of acetopropanol to DHMF, or both.

* * * * *

UNITED STATES PATENT AND TRADEMARK OFFICE
CERTIFICATE OF CORRECTION

PATENT NO. : 6,045,662

DATED : April 4, 2000

INVENTOR(S): Wolfgang KLEEMISS et al

It is certified that an error appears in the above-identified patent and that said Letters Patent is hereby corrected as shown below:

Column 1, line 10, "4,5-dihydro-2-methylfaran" should read --4,5-dihydro-2-methylfuran--.

Column 5, line 25, "into the k-k-k-- distillation" should read --into the distillation--.

Column 5, line 34, "approximately 150 gfh." should read --approximately 150 g/h.--.

Column 5, line 38, "Refklux (Rk/D):" should read --Reflux (R/D):--.

Column 5, line 65, "gk/h)" should read --g/h)--.

Column 6, line 65, Claim 1, "(CPMT()" should read --(CPMK)--.

Signed and Sealed this

Fifteenth Day of May, 2001

Attest:

NICHOLAS P. GODICI

Attesting Officer          Acting Director of the United States Patent and Trademark Office